United States Patent
Doherty et al.

(10) Patent No.: US 10,913,025 B2
(45) Date of Patent: Feb. 9, 2021

(54) REMOVAL OF DUST IN UREA FINISHING (71) Applicant: Stamicarbon B.V., Sittard (NL)

(72) Inventors: Cain Christopher Doherty, Sittard (NL); Aloysius Mechteldis Emmanuel Schoenmakers, Sittard (NL)

(73) Assignee: Stamicarbon B.V., Sittard (NL)

( * ) Notice: Subject to any disclaimer, the term of this patent is extended or adjusted under 35 U.S.C. 154(b) by 520 days.

(21) Appl. No.: 15/536,077

(22) PCT Filed: Dec. 17, 2015

(86) PCT No.: PCT/NL2015/050873
§ 371 (c)(1),
(2) Date: Jun. 14, 2017

(87) PCT Pub. No.: WO2016/099267
PCT Pub. Date: Jun. 23, 2016

(65) Prior Publication Data
US 2018/0326345 A1 Nov. 15, 2018

(30) Foreign Application Priority Data
Dec. 19, 2014 (EP) ..................... 14199372

(51) Int. Cl.
*B01D 47/05* (2006.01)
*B01D 47/06* (2006.01)
*B01D 47/10* (2006.01)
*C05C 9/00* (2006.01)
*C07C 273/04* (2006.01)
*C07C 273/02* (2006.01)

(52) U.S. Cl.
CPC ............. *B01D 47/10* (2013.01); *B01D 47/05* (2013.01); *B01D 47/06* (2013.01); *C05C 9/00* (2013.01); *C07C 273/02* (2013.01); *C07C 273/04* (2013.01)

(58) Field of Classification Search
CPC ........ B01D 47/05; B01D 47/06; B01D 47/10; C05C 9/00; C07C 273/02; C07C 273/04
See application file for complete search history.

(56) References Cited

U.S. PATENT DOCUMENTS

| | | | |
|---|---|---|---|
| 3,798,021 A | * | 3/1974 | Bress .................. C05C 1/00 71/28 |
| 4,104,041 A | | 8/1978 | Arita et al. |
| 5,176,723 A | * | 1/1993 | Liu .................. B01D 47/05 95/216 |

OTHER PUBLICATIONS

International Search Report for PCT/NL2015/050873, dated May 30, 2016, 3 pages.

* cited by examiner

*Primary Examiner* — Cabrena Holecek
(74) *Attorney, Agent, or Firm* — Morrison & Foerster LLP (57) ABSTRACT

Disclosed is a method for the removal of urea dust from the off-gas of a finishing section of a urea production plant. the method comprises subjecting the off-gas to quenching with water so as to produce quenched off-gas. The quenched off-gas is subjected to humidification by mixing said quenched gas stream with a humidification fluid selected from (a) saturated steam and (b) superheated steam mixed with a second aqueous stream, so as to produce a humidified gas stream, subjecting said humidified gas stream to particle separation (i.e., dust removal) by means of a scrubbing liquid in which at least part of the particles in the gas stream are soluble.

6 Claims, 4 Drawing Sheets

REMOVAL OF DUST IN UREA FINISHING

CROSS-REFERENCE TO RELATED APPLICATIONS

This application is the national phase of PCT application PCT/NL2015/050873 having an international filing date of 17 Dec. 2015, which claims benefit of European patent application No. 14199372.5 filed 19 Dec. 2014. The contents of the above patent applications are incorporated by reference herein in their entirety.

FIELD OF THE INVENTION

The invention is in the field of urea production, and pertains to the removal of urea dust from the off-gas associated with the production of solid urea particles (urea finishing). Particularly, the invention pertains to the reduction of the emission of urea dust occurring from such a urea plant finishing section. The invention also pertains to a urea production plant, and to revamping an existing urea production plant.

BACKGROUND OF THE INVENTION

Urea is produced from ammonia and carbon dioxide. Today's urea production involves relatively clean processes, particularly low in the emission of urea dust and ammonia. However, besides the chemical synthesis of urea, the production of urea on a commercial scale requires that the urea be presented in a suitable solid, particulate form. To this end, urea production involves a finishing step in which a urea melt is brought into the desired particulate form, generally involving any one of prilling, granulation, and pelletizing.

Prilling used to be the most common method, in which the urea melt is distributed, as droplets, in a prilling tower and whereby the droplets solidify as they fall down. However, the end-product is often desired to have a larger diameter and higher crushing strength than the one resulting from the prilling technique. These drawbacks led to the development of the fluidized bed granulation technique, where the urea melt is sprayed on granules that grow in size as the process continues. Prior to the injection in the granulator, formaldehyde is added to prevent caking and to increase the strength of the end-product.

In order to remove the energy released during crystallization, large amounts of cooling air are fed to the finishing unit. The air that leaves the finishing section contains, inter alia, urea dust. With a view to increased demand for urea production, and increasing legal and environmental requirements as to reduce the level of emissions, it is desired that the urea dust is removed, and according to ever increasing standards.

Over the past several decades the control of air pollution has become a priority concern of society. Many countries have developed highly elaborate regulatory programs aimed at requiring factories, and other major sources of air pollution, to install the Best Available Control Technology (BACT) for removing contaminants from gaseous effluent streams released into the atmosphere. The standards for air pollution control are becoming increasingly stringent, so that there is a constant demand for ever more effective pollution control technologies. In addition, the operating costs of running pollution control equipment can be substantial, and so there is also a constant demand for more efficient technologies.

The removal of urea dust is challenging per se, since the amounts of off-gas (mainly air) are enormous, whilst the concentration of urea dust is low. A typical airstream is of the order of 750 000 $Nm^3/h$. A typical concentration of urea dust therein is about 0.5-1 wt. %. Further, part of the urea dust is of a submicron size. Satisfying current standards implies the need to remove a major part of this submicron dust.

A further problem is that the large amounts of air needed in urea finishing, results in this part of the production process being a relatively costly effort due to the need for very large extractor fans having a high electricity consumption. Particularly, when the air is subjected to scrubbing in order to reduce the emission of urea dust, and specifically a major part of the submicron dust, into the atmosphere, a relatively large amount of energy is simply lost in the process, as a result of the inevitable pressure drop in the scrubbing device.

In the art it is acknowledged that aerosol-particles (in the sub-micron and micron size range as is typical for urea dust) grow due to condensation of water on them from supersaturated gas that surrounds such particles. If the gas surrounding the aerosols/particles is saturated or sub-saturated, but not supersaturated, there is no growth or even negative growth of water from the wet surface of the aerosol-particle. As a result, the particle remains the same size or even evaporation from the surface of the particle occurs. The general belief is that the degree of supersaturation (known as a factor S) needs to be larger than unity (1) to obtain condensation of water on aerosols, which is imperative to obtain growth of particles. Throughout the art on removing sub-micron dust particles, it is acknowledged that effective removal requires an atmosphere in which water vapor is present in a supersaturated state.

Specifically in the art of urea finishing, such as in urea-granulation technology, it is recognized that it is impossible, in practice, to obtain a supersaturated gas-stream downstream of the finishing step. This can be explained with reference to the large amount of relatively dry air, and thus low presence of amounts of water, that are naturally present in the off-gas from urea finishing (e.g. from the granulator). In fact, the system initially (in the finishing section) starts from almost zero saturation, i.e., too strongly an undersaturated situation to reach a level of saturation, let alone supersaturation.

Condensation scrubbing is a relatively recent development in wet scrubber technology. Most conventional scrubbers rely on the mechanisms of impaction and diffusion to achieve contact between the particulate matter (PM) and liquid droplets. In a condensation scrubber, the PM acts as condensation nuclei for the formation of droplets. Generally, condensation scrubbing depends on first establishing saturation conditions in the gas stream. Once saturation is achieved, steam is injected into the gas stream. The steam creates a condition of super-saturation and leads to condensation of water on the fine PM in the gas stream. The large condensed droplets are then removed by one of several conventional devices, such as a high efficiency mist eliminator. [Air Pollution Control Technology Fact Sheet EPA-452/F-03-010].

A background reference on the application, in industrial dust collection, of particle enlargement by condensation, is Yoshida et al., Journal of Chemical Engineering of Japan, 1978, Vol. 11, No. 6, p. 469-475. Herein humidification of a gas stream is brought about by steam injection. This is taught to be especially effective for low temperature gas.

Another such background reference is EP 555 474. Herein a process is disclosed for cleaning a gas stream by enlarging and collecting dust particles through vapor nucleation and inertial condensation on a cooler.

A further reference relating to the removal of dust from a gas stream is FR 2600553. Herein an improved gas-washing (scrubbing) process is described. In a first washing step, a washing fluid is sprayed into the gas stream, in a direction countercurrent to that of the gas stream (which is the conventional direction in a washing operation). The gas stream is thereafter passed through a plurality of parallel venturi nozzles, subjected to liquid/gas separation, and passed through a sprayed washing fluid.

A reference directed to cleaning gas mixtures which might contain dust from a urea plant is EP 0 084 669. Disclosed is applying an aqueous washing solution to which formaldehyde is added before it is brought in contact with the gas mixture. The method as disclosed specifically pertains to the addition of formaldehyde, and is carried out using standard scrubbers.

U.S. Pat. No. 3,985,523 concerns the removal of contaminants from air generated in the production of fertilizers. Disclosed is a process wherein contaminated vapor is condensed and a resulting liquid contaminant stream is further treated.

Of particular concern to those in the field of air pollution control is the reduction of emitted "fine particulate" due to the adverse health effects associated with both long-term and short-term respiratory exposure to fine particulate. As used herein, the term "fine particulate" should be understood to mean particles having a diameter smaller than 2.5 µm. In an effort to control these particles, the EPA has recently reduced the "PM2.5 standards" for the emissions of particles less than 2.5 µm. These small particles are difficult to collect in conventional scrubbers due to their size. Nonetheless, particles in this size range are currently responsible for the measured emissions.

Urea dust is soluble in water. When solid particles of urea are captured in water, they fully or partially dissolve into a solution of water and urea. As increasingly more urea is captured in water, the concentration of dissolved urea will increase until a solubility limit is reached and no further urea will be dissolved. As thermodynamic conditions change, urea can also precipitate out of solution, forming solid particles. When capturing urea dust in a scrubber, it is beneficial to concentrate and control the urea concentration of the solution so that the captured urea can be beneficially reused.

The prior art does not relate to processes by which condensation scrubbing of off-gas from urea finishing can be suitably conducted. Particularly, the prior art does not teach how to overcome the problem that in urea finishing, such as in urea-granulation technology, it has been recognized to be impossible, in practice, to obtain a supersaturated gas-stream downstream of the finishing step, let alone to reach supersaturation.

It is now desired to provide a method for treating the off-gas of a urea finishing section in such a way as to effectively remove urea dust. It is further desired to provide a method by which this removal is improved. And, moreover, it is desired to achieve this in a process of improved energy efficiency.

SUMMARY OF THE INVENTION

In order to better address one or more of the foregoing desires, the invention, in one aspect, presents a method for removing particles (also indicated as particulate matter or dust) from a gas stream obtained from a finishing section of a urea production plant, the method comprising quenching said gas stream using a first aqueous stream so as to create a quenched gas stream; mixing said quenched gas stream with a humidification fluid selected from (a) saturated steam and (b) superheated steam mixed with a second aqueous stream, so as to produce a humidified gas stream, subjecting said humidified gas stream to particle separation (i.e., dust removal) by means of a scrubbing liquid in which at least part of the particles in the gas stream are soluble.

In another aspect, the invention provides a finishing equipment for a urea plant, said finishing equipment comprising a urea finishing device comprising an inlet for liquid urea, an inlet for cooling gas, a collector for solid urea, an outlet for off-gas, said outlet being in fluid communication with a gas treatment section comprising, in downstream order, a quenching zone provided with an inlet for a quenching liquid, a humidification zone comprising an inlet for steam or for steam mixed with an aqueous stream, and a particle removal system (also indicated as a dust removal system) comprising an inlet for a scrubbing liquid and an outlet for an aqueous stream with dissolved particles.

In a further aspect, the invention concerns a urea plant comprising a synthesis and recovery section; said section being in fluid communication with an evaporation section, said evaporation section being in fluid communication with a finishing section and having a gas flow line to a condensation section; wherein said finishing section has a gas flow line to a gas treatment section comprising, in downstream order, a quenching system provided with an inlet for a quenching liquid, a humidification system comprising an inlet for steam or for steam mixed with an aqueous stream, and a particle removal system comprising an inlet for a scrubbing liquid and an outlet for an aqueous stream with dissolved particles.

In yet another aspect, the invention presents a method of modifying an existing urea plant, said plant comprising a synthesis and recovery section (A); said section being in fluid communication with an evaporation section (B), said evaporation section being in fluid communication with a finishing section (C) and having a gas flow line to a condensation section (E); said finishing section (C) having a gas flow line to a dust scrubbing section (D), wherein one modifies the plant by placing, between the finishing section (C) and the dust scrubbing section (D), a gas treatment section comprising, in downstream order, a quenching system (F) provided with an inlet for a quenching liquid, and a humidification system (G) comprising an inlet for steam or for steam mixed with an aqueous stream, and a gas outlet that is in fluid communication with said dust scrubbing section (D).

DETAILED DESCRIPTION OF THE INVENTION

In a broad sense, the invention is based on the judicious insight to purify the off-gas of a urea finishing section by subjecting it to a double treatment, viz. quenching and humidification. Particularly, the invention is based on the judicious insight to thereby apply a humidification fluid selected from (a) saturated steam and (b) superheated steam mixed with an aqueous stream. An advantage of the treatment of the invention is that the humidification can be conducted so as to bring about saturation of the off-gas, despite the dry nature thereof. This has hitherto not been conceivable in the art for a dry gas stream such as the off-gas from a finishing section of a urea plant. More particularly, the gas stream to be treated is an exhaust gas stream from a fluid bed granulator or a prilling tower in a urea production process. However, the inventors believe that the method is also applicable to other gas streams having the same dry character. Thus, the invention can also be applied to other gas streams that are substantially water free, such as having less than 1% of water.

The first step of the aforementioned double treatment is quenching. It is noted that, as the skilled person will understand, quenching of a gas stream is fundamentally different from washing. The purpose of quenching is to condition the gas stream, particularly by generating an atmosphere having a 100% relative humidity (RH). Typically, this is done by spraying a quenching liquid co-currently with the gas stream, and/or to provide a quenching chamber wherein the gas and the quenching liquid are subjected to a residence time that is sufficiently long for the gas to be conditioned at, or at least close to 100% RH. A washing (or scrubbing) operation, on the other hand, is not related to conditioning an atmosphere, but to bring about a physical contact between a gas to be washed (i.e. scrubbed) and a washing liquid, after which an immediate removal of the washing liquid is normally foreseen. Typically, therefore, the washing (scrubbing) of a gas stream involves contacting the gas with a counter-current or cross-current flow of a washing liquid.

It will also be understood that liquids used for washing a gas stream, due to the different purpose of the liquid, are not applied in such a way as to induce quenching of the gas.

Quenching refers to adding water to the off-gas. This is generally done by one or more quenchers, i.e. devices that serve to introduce water into the gas stream. This introduction will generally be done in such a way that the water is well-dispersed into the gas. Preferably, the water is introduced into the gas by spraying it into the gas flow line between the finishing section and the dust scrubbing section. This can be done by spraying liquid into a duct just preceding the dust scrubbing section. It can also be a separate chamber or tower equipped with a spray system. Spray systems, suitable atomization nozzles, and the like, are known to the skilled person. Preferably, the liquid is sprayed in such a way and consistency that liquid droplets are formed that are so small that the droplets evaporate quickly and a liquid saturation in the vapor near equilibrium is reached within a short time. The quenching can be done as a single operating step, or in two or more stages. In such stages, the quenching liquids can be the same or different.

The quenching, as applied in the present invention, of the off-gas from a finishing section of a urea plant, also results in cooling down the gas. This is preferably to a temperature below about 45° C. and creating a liquid saturation near equilibrium. Preferably, the liquid is sprayed in such a way and consistency that liquid droplets are formed that are so small that the droplets evaporate quickly, and a liquid saturation in the vapor near equilibrium is reached within a short time. For completeness' sake, it is noted that spraying the aqueous quenching liquid only, does not lead to complete saturation, let alone supersaturation.

Preferably the quenching stream (i.e., the first aqueous stream) has a temperature of below 45° C., more preferably below 40° C., most preferably below 35° C. The typical air temperature of the off-gas exiting a finishing section of a urea plant, such as in fluid bed granulation, is about 100° C. After quenching, the temperature is preferably below 45° C. Accordingly, the temperature of the gas stream is lowered by typically more than 50° C., preferably more than 60° C., and most preferably more than 65° C. It will be understood that in the event of gas streams other than off-gas from urea finishing, the absolute temperature values can be different. Further, the skilled person will understand that the cooling depends on the amount of liquid which can be evaporated. This is determined by the temperature and water vapor content of the off-gas to be quenched.

The quenching liquid will generally be a re-used process liquid, either from a nearby installation or a plant coupled to the plant in which the gas stream is to be treated, or from a different part of the same plant. More preferably, the quenching liquid is re-circulated from the gas treatment itself, as explained below.

The second step of said double treatment is humidification, by applying either saturated steam or superheated steam mixed with an aqueous stream. The humidification of the quenched gas stream allows bringing about saturation of the gas stream. Preferably, therefore the humidification is, in fact, saturation.

A next step comprises subjecting the humidified, preferably saturated gas stream to particle separation. This is done, in one or more steps, by means of a scrubbing liquid in which at least part of the particles in the gas stream are soluble. Typically, the scrubbing liquid is water or an acidified solution, such as a solution acidified with for example sulphuric acid.

All or at least part of the captured particulate matter dissolves in the scrubbing liquid. Typically, 0.1 wt. % to 99.9 wt. % of the captured soluble particulate dissolves in the quenching liquid. Preferably, at least 50 wt. % of the captured particulate dissolves in the scrubbing liquid, e.g. 50 wt. % to 95 wt. %, preferably 80 wt. % to 95 wt. %.

In an interesting embodiment, the first aqueous stream, i.e., the stream used as a quenching liquid, comprises dissolved particles which are the same as the particles to be removed from the gas stream. Preferably, thereby the quenching liquid comprises an aqueous liquid recycled from the scrubbing step. This refers to an aqueous stream obtained from scrubbing the humidified gas stream. This stream will comprise dissolved particles as a result of the removal of dust from the scrubbed gas stream. Without wishing to be bound by theory, the inventors believe that the presence of dissolved particles in the quenching liquid will aid the growing of such particles when further dust particles are retrieved from the gas stream. This, in turn, facilitates the removal of such dust particles from the gas stream.

A further interesting embodiment relates to the aforementioned option (b), whereby the humidification fluid comprises superheated steam mixed with a second aqueous stream. In this embodiment it is preferred that said second aqueous stream has the same composition as the first aqueous stream.

In a further preference hereof, both the first and the second aqueous stream comprise dissolved particles which are the same as the particles to be removed from the gas stream. In that event, both of these streams preferably comprise an aqueous liquid recycled from the scrubbing liquid, i.e., the liquid obtained after the step of scrubbing of the humidified gas stream. Thereby the second aqueous stream, i.e. the stream used in the humidification step, preferably has a lower concentration of dissolved particles than the first aqueous stream.

In the event of the treatment of a gas stream obtained as off-gas from a urea finishing section, typically ammonia is present in the gas stream to be treated. Further, typically dissolved ammonium salts, traces of acid, or both, are present in the aqueous stream obtained after scrubbing, particularly as generated by acidic scrubbing of the humidified gas stream.

In an interesting embodiment, the particle separation comprises one or more venturi scrubbing steps. A venturi scrubber is a well known type of device for removing contaminants from a gaseous effluent stream. venturi scrubbers are generally recognized as having the highest fine particle collection efficiency of available scrubbing devices. In a venturi scrubber the effluent gas is forced or drawn through a venturi tube having a narrow "throat" portion. As the air moves through the throat it is accelerated to a high velocity. A scrubbing liquid in the form of droplets, typically of water, is added to the venturi, usually at the throat, and enters the gas flow. The water droplets used are generally many orders of magnitude larger than the contaminant particles to be collected and, as a consequence, accelerate at a different rate through the venturi. The differential acceleration causes interactions between the water droplets and the contaminant particles, such that the contaminant particles are collected by the water droplets. The collection mechanisms involve, primarily, collisions between the particles and the droplets and diffusion of particles to the surface of the droplets. In either case, the particles are captured by the droplets. Depending on the size of the contaminant particles, one or the other of these mechanisms may predominate, with diffusion being the predominant collection mechanism for very small particles, and collision or interception being the predominant mechanism for larger particles. A venturi scrubber can also be efficient at collecting highly soluble gaseous compounds by diffusion. A detailed description of these scrubbing mechanisms is discussed in Chapter 9 of Air Pollution Control Theory, M. Crawford, (McGraw-Hill 1976).

Where it is spoken of "venturi scrubber" this can refer to either a single venturi scrubber or a plurality of venturi scrubbers. Further, one or more venturi scrubbers can themselves comprise one or more venturi tubes.

Where, in this description, it is spoken of "fluid communication", this refers to any connection between a first part or section of a plant and a second part or section of a plant via which fluids, notably liquids, can flow from the first part of the plant to the second part of the plant. Such fluid communication is typically provided by piping systems, ducts, hoses, or other devices well-known to the skilled person for the transportation of fluids.

Where in this description it is spoken of "gas flow lines" this refers to any connection between a first part or section of a plant and a second part or section of a plant via which gas or vapors, notably aqueous vapors, can flow from the first part of the plant to the second part of the plant. Such gas flow lines typically comprise piping systems, ducts or other devices well-known to the skilled person for the transportation of gases, if needed under above or below (vacuum) atmospheric pressures.

When in this description it is spoken of "zone" or "section" this refers to generally the same thing, viz. a part of an industrial installation, where certain defined events occur. Such a part may also be indicated with the term "system."

The invention particularly pertains to urea finishing. This part of a urea production process refers to the section where solid urea is obtained.

Figure 1:
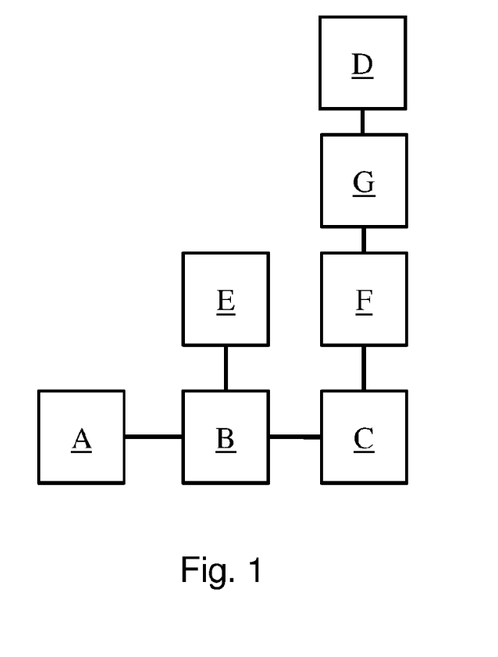
FIG. 1 depicts a block diagram of a urea plant provided with a gas treatment section according to the invention.

As an example, a schematic drawing of a plant having a finishing section in accordance with the invention is depicted in FIG. 1. For convenience, parts of the plant discussed below refer to the elements contained in FIG. 1. This does not imply that any plant built in accordance with the invention needs to be in accordance with FIG. 1.

This finishing section, section (C) in FIG. 1, may be a prilling tower, granulation section, pelletizing section, or a section or equipment based on any other finishing technique. A granulation section may be a fluidized bed-granulation, or a drum granulation, or a pan-granulation, or any other similar and known granulation device. The main function of this finishing section is to transfer a urea melt, as obtained from urea synthesis, into a stream of solidified particles. These solidified particles, usually prills, granules or pellets, is the main product stream from the urea plant. In any event, to transfer the urea from the liquid phase into the solid phase, the liquid has to be cooled down to the crystallization temperature and the heat of crystallization has to be removed. Moreover, usually some additional heat is removed from the solidified urea particles, in order to cool them to a temperature that is suitable for further processing and handling, including safe and comfortable storage and transport of this final product. The resulting removal of the total amount of heat for cooling the liquid to crystallization temperature, for transfer from liquid into solid phase and for subcooling of the solid particles in the finishing section, is usually done by air picking up heat and leaving the finishing section at a temperature higher than the inlet temperature. Liquid sprayed into the air evaporates before the air enters the zone in which solidification takes place. It cools down the air, and this way it decreases the air requirement.

Usually most of the crystallization/cooling heat is removed by cooling with air. The cooling air, by nature of the cooling process, leaves the finishing section at an increased temperature. Usually an amount of air equal to 3-30 kg of air per kg of final solidified product is applied, preferably 3-10 kg. This is the typical off-gas of the finishing section of a urea production plant.

In the finishing section (C), the air comes into direct contact with the urea melt and with the solidified urea particles. This inadvertently leads to some contamination of the air with some urea dust, and ammonia. Depending on the nature of the finishing section (prilling/granulation, type of granulation, conditions selected in granulation), the amount of dust present in the air may vary widely, values being in the range of 0.05% to 10% by weight (with respect to the final product flow) having been observed. For a finishing section based on granulation, the amount of dust more typically is in a range of from 2% to 8% by weight. This presence of dust in the off-gas usually makes a dust removal system (D) required, either for environmental or from economical considerations, before the air can be vented back into the atmosphere.

In the dust scrubbing section (D), dust scrubbing is usually done using a circulating urea solution as a washing agent. On top of this also fresh water scrubbing usually is applied. In the dust scrubbing section D a purge flow of urea solution is obtained. This purge flow usually has a concentration of 10-60% (by wt.) of urea. In order to reprocess the urea present in this purge flow, the purge flow is returned to the evaporation section (B), where it is further concentrated and then recycled to the finishing section (C). Cleaned air is vented from the dust scrubbing into the atmosphere. In the dust scrubbing section, e.g., one or a combination of the following wet scrubbing technologies can be applied: spray chamber scrubbing, packed bed scrubbing, impingement plate scrubbing, mechanically-aided scrubbing, venturi scrubbing, orifice scrubbing, condensation scrubbing, charged scrubbing, fiber-bed scrubbing.

A quench zone employing spray quenchers will preferably comprise (a) a section in which the gas to be quenched is cooled by the introduction (e.g. injection) and evaporation of water; (b) a particulate matter (dust) capture basin, serving to collect dust stripped from the gas; (c) a sprayer system consisting of lances equipped with injection nozzles, and (d) a water supply system with pumps.

Before makeup water is added to the aqueous quenching liquid, the solution concentration is generally allowed to cycle up by recirculation of the quenching liquid. The latter is also a standard choice for the skilled person seen from process economy. Generally, quenching liquid is re-circulated until the dissolved particulate solution reaches a concentration of up to 50% by weight before it is extracted or bled off. In practice, a portion of the circulating fluid is continuously extracted containing the desired concentration of the dissolved particulate matter. This extracted liquid is sometimes called the purge or blow-down. At the same time, the remaining liquid is diluted by addition of makeup water which can be fresh water or a more diluted stream (e.g., from a section downstream of the quench).

The off-gas (or "gaseous effluent") coming from the finishing section, e.g. from a prilling tower or fluid bed granulator, is intended to include effluent streams that have liquid or solid particulate material entrained therein, including vapors which may condense as the effluent stream is cooled.

In the quench zone, the gaseous effluent is cooled to a much lower temperature, preferably below about 45° C. Many methods of cooling a hot effluent gas flow are known to those skilled in the art.

A preferred method for use in the invention involves spraying a cooling liquid such as water, into the gas through nozzles. Without wishing to be bound by theory, the inventors believe that spray-quenching contributes to the efficient removal of dust, by allowing water to interact with dust particles.

This is an unexpected benefit of spray-quenching. In the art, not related to urea but, e.g., to flue gas, cooling of a gaseous effluent has an effect in supersaturated systems. Therein, cooling the effluent causes condensable vapors in the effluent stream to undergo phase transition. Condensation of these vapors will naturally occur around particles in the effluent stream which serve as nucleation points. Pre-cooling the effluent stream is, thus, useful for two reasons. First condensable contaminants are transformed to the liquid phase and are thereby more easily removed from the effluent. Second, the nucleation process increases the size of pre-existing particles in the effluent, thereby making it easier to remove them.

The removal of the larger particles by quenching prevents the larger particles from competing with the submicron particles as nucleation sites. As mentioned above, it is desirable that the submicron particles increase in size due to condensation so that they are easier to remove from the effluent flow.

A problem with the gaseous effluent treated in the invention, i.e. the off-gas of a finishing section of a urea plant, is that it is in a subsaturated state. As the sole condensable vapor, the off-gas contains a limited amount of water. As a result, it would have to be cooled down to much lower values than achievable by quenching in order to have water condense as desired. It is noted that it is fundamentally impossible to cool down the off-gas, by quenching only, to such a low temperature that condensation of water vapor will occur, because heat is only removed by evaporation of water. Starting from a subsaturated state, quenching can lower the temperature and increase the water vapour content of the off-gas only until the point of full saturation. This point of equilibrium between off-gas and quenching liquid cannot be crossed, or in other words supersaturation cannot be achieved.

The invention solves this by introducing the additional step of humidification.

The quenched and humidified gas is led to a particle capture zone. A "particle capture zone" refers to a section in which the gas is subjected to conditions serving the removal of particulate matter therefrom. Typically, this refers to a particle capture vessel such as a wet scrubber. It can also refer to, e.g., a venturi scrubber or a wet electrostatic precipitator (WESP). In a preferred embodiment, the particle capture zone comprises a combination of, in series, a wet scrubber (such as a tray scrubber) and, downstream thereof, a venturi scrubber. More preferably, the venturi scrubber comprises a plurality of venturi tubes in parallel. In another preferred embodiment, a WESP is positioned downstream of the wet scrubber, or downstream of the venturi scrubber, or most preferably in series after the wet scrubber and the venturi scrubber.

The invention also pertains to the equipment for carrying out the above-described method. This refers to a finishing system for a urea plant. Therein a urea finishing device is present comprising the appropriate attributes to perform its function. These attributes are known to the skilled person, and generally include an inlet for liquid urea, an inlet for cooling gas, a collector for solid urea (typically: urea particles, preferably granules), and an outlet for off-gas. The outlet for off-gas is in fluid communication (typically via a gas flow line) with the inlet of a gas treatment section comprising, in downstream order, a quenching system provided with an inlet for a quenching liquid, a humidification system comprising an inlet for steam, or a mixture of steam and an aqueous stream, and a particle removal system comprising an inlet for a scrubbing liquid and an outlet for an aqueous stream with dissolved particles.

In one embodiment, the steps of quenching and humidification are carried out in sequence, but in the same equipment. In another embodiment, these steps are carried out in separate equipment.

In a preferred embodiment, the particle removal system comprises a plurality of venturi scrubbers, operated in parallel. Preferably, the dust removal system is so designed that these parallel venturi tubes can be operated independently of each other, i.e. the number of venturi tubes used at the same time, can be adapted during the process as desired. A preferred system is that provided by Envirocare.

Envirocare scrubbers consist of a quenching section, downstream of which a so-called MMV-section (micro-mist venturi) is installed. The MMV-section consists of multiple parallel venturis. In the MMV-section large quantities of liquid are sprayed in the throat of the venturis co-currently with the gas-flow through single phase nozzles, creating a consistent and adjustable liquid droplet-size, typically in a range of from 50 µm to 700 µm. The liquid droplet size is one of the parameters that can be used to control the efficiency of dust-removal The invention also pertains to a urea plant comprising a finishing section as described above. More particularly, the urea plant of the invention, as illustrated in the example of FIG. 1, comprises a synthesis and recovery section (A); which is in fluid communication with an evaporation section (B). The evaporation section is in fluid communication with a finishing section (C), and has a gas flow line to a condensation section (E). The finishing section (C) has a gas flow line to a gas treatment section comprising, in downstream order, a quenching system provided with an inlet for a quenching liquid (F), a humidification system (G) comprising an inlet for steam, or a mixture of steam and an aqueous stream, and a particle removal system (D) comprising an inlet for a scrubbing liquid and an outlet for an aqueous stream with dissolved particles.

In a preferred embodiment, the dust scrubbing section comprises at least one venturi scrubber (D), and the quenching system preferably comprises a spray-quencher (F). The quenching system is installed between the finishing section (C) and the venturi scrubber (D), and is in fluid communication with the gas flow line between the finishing section (C) and the humidification section (G). Preferably, a plurality of venturi scrubbers is employed as outlined above. It will be understood that any desired number of venturis is in fluid communication (typically via a gas flow line) with the gas outlet of the finishing section.

The invention is applicable to the construction of new urea plants ("grass root" plants) as well as in revamping existing urea plants.

It will be understood that a new plant according to the invention can just be built in conformity with the above. In revamping existing plants, the invention pertains to a method of modifying an existing urea plant, in such a way as to ensure that the plant has a gas treatment section provided with, in downstream order, a quenching system provided with an inlet for a quenching liquid, a humidification system comprising an inlet for steam, or a mixture of steam and an aqueous stream, and a particle removal system comprising an inlet for a scrubbing liquid and an outlet for an aqueous stream with dissolved particles.

Hereinafter several embodiments of the invention will be discussed with reference to the drawings. It will be understood that the invention is not limited to the embodiments shown in any of the drawings. Accordingly, the following descriptions of embodiments, whilst discussing the components shown in FIGS. 1 to 5 are also applicable to other embodiments, not necessarily as shown.

As an example, a schematic drawing of a plant having a finishing section in accordance with the invention is depicted in FIG. 1. The block diagram in FIG. 1 shows a urea plant comprising (A) a synthesis and recovery section. Said section is in fluid communication with an evaporation section (B). The evaporation section is in fluid communication with a finishing section (C), and has s gas flow line to a condensation section (E). The finishing section (C), which can comprise, e.g. a prilling tower, a granulation section, a pelletizing section, or a section or equipment based on any other finishing technique. A granulation section may be a fluidized bed-granulation, or a drum granulation, or a pan-granulation, or any other similar and known granulation device. Conventionally, the finishing section (C) would have a gas flow line to a dust scrubbing section (D). The plant according to FIG. 1 has been modified in accordance with the invention. As a result, between the finishing section (C) and the dust scrubbing section (D), a gas treatment section is placed. Said gas treatment section comprises, in downstream order, a quenching section (F) provided with an inlet for a quenching liquid, and a gas outlet to a humidification section (G). The humidification section (G) comprises, in addition to a gas inlet connected to the gas outlet of the quenching section, an inlet for steam, or for a mixture of steam and an aqueous stream, and a gas outlet that is in fluid communication with said dust scrubbing section (D).

Figure 2:
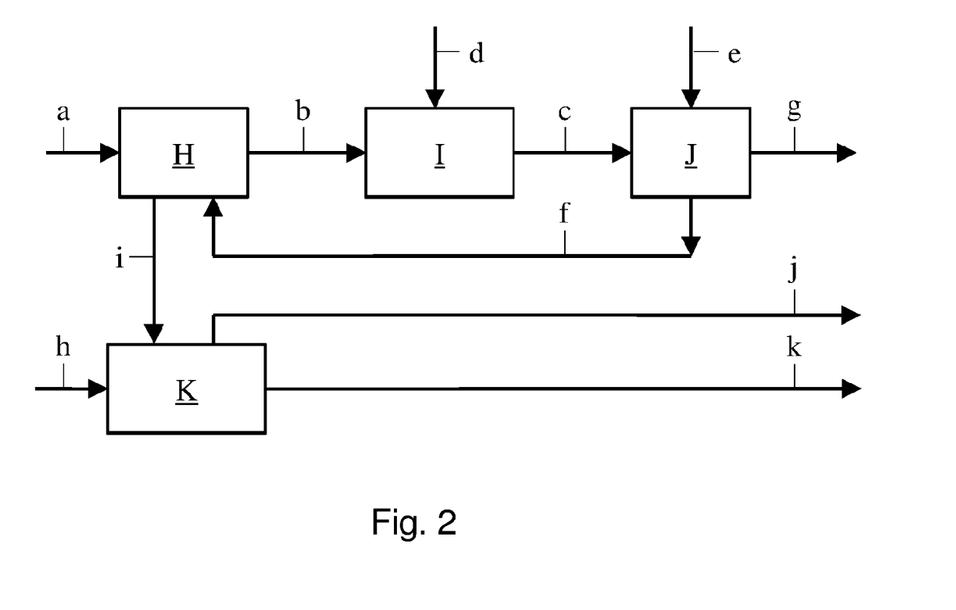
FIGS. 2-6 depict flow schemes of embodiments of a process according to the invention.

FIGS. 2-6 provide further detailed schemes of process embodiments of the invention. The legend to FIGS. 2-5 is as follows:
Sections:
H. Quenching zone;
I. Humidification zone;
J. Particle removal zone;
K. Evaporation zone;
Streams:
(a) gas with dust particles, 100° C., low humidity;
(b) quenched gas 45° C., 80% RH;
(c) humidified gas;
(d) saturated steam;
(e) process water;
(f) water with dissolved particles;
(g) gas to atmosphere;
(h) heat;
(i) aqueous stream from quench
(j) vapor;
(k) concentrated solution;
(l) superheated steam;
(m) aqueous stream;
(n) water with reduced concentration of dissolved particles;
(o) water with increased concentration dissolved particles;

It is shown that gas with dust particles, of a temperature of 100° C. and of low humidity (typically a dry off-gas, of relatively low temperature, of a finishing section of a urea production plant) is fed to a gas treatment section. This involves first subjecting the gas to a quench, whereby the gas becomes cooled down to 45° C. and whereby the relative humidity (RH) of the quenched gas is increased to 80% RH. This quenched gas is then subjected to humidification, thereby bringing about saturation. In the embodiment of FIG. 2, this is by being brought into contact with saturated steam.

As the skilled person will understand, the amount of steam (i.e., the ratio of steam to gas) mainly depends on the degree of saturation which can be achieved in the preceding quench. A typical range is 0.5-5% relative to the amount of gas (air), e.g. by weight. By way of guidance in the form of an example: in the event that the water concentration in the blowdown/purge stream is fixed at, e.g., 55%, the RH of the gas leaving the quench is 80.6%. Then 3116 kg/h of steam is required, which is 3% relative to the amount of gas (air). At 80% water concentration, the RH of the gas is 93.5% and only 736 kg/h of stem is required to achieve 100% saturation. 736 kg/h is 0.7% relative to the amount of gas.

Figure 3:
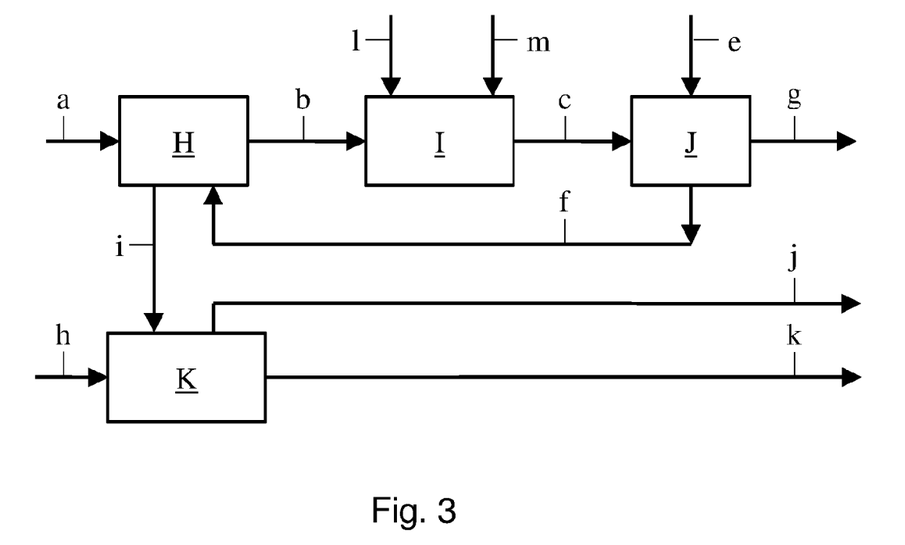

In the embodiment of FIG. 3, this is by being brought into contact with superheated steam and with an aqueous stream (i.e., a second aqueous stream). The superheated steam will generally have a temperature in a range of from 125° C. to 250° C., more typically from 140° C. to 200° C. The amount of said second aqueous stream will generally vary between 5% and 15% relative to the superheated steam, more typically from 7% to 12%.

The resulting humidified (and saturated) gas stream is then subjected to the removal of dust particles, by scrubbing with process water, i.e, with a stream recycled from elsewhere in the plant (in the event of a urea plant, the water supplied to the scrubbing system typically is a condensate from the wastewater treatment).

The resulting scrubbed gas is sent into the atmosphere. The obtained scrubbing liquid, in this embodiment, is recycled to the quenching section, and used as a quenching liquid.

Figure 4:
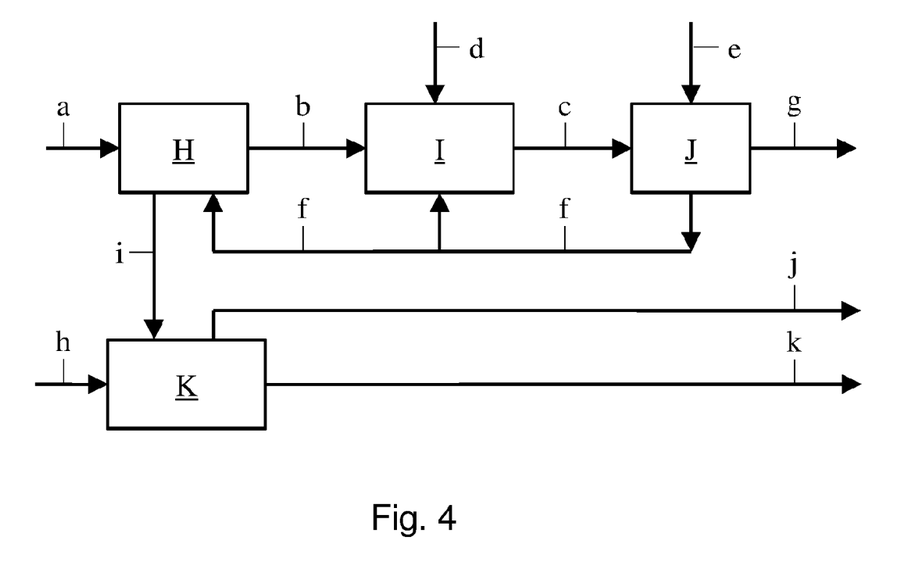

In FIG. 4, the above-mentioned second aqueous stream applied in the humidification section, is the same recycled stream of the scrubbing liquid as used in the quenching section.

Figure 5:
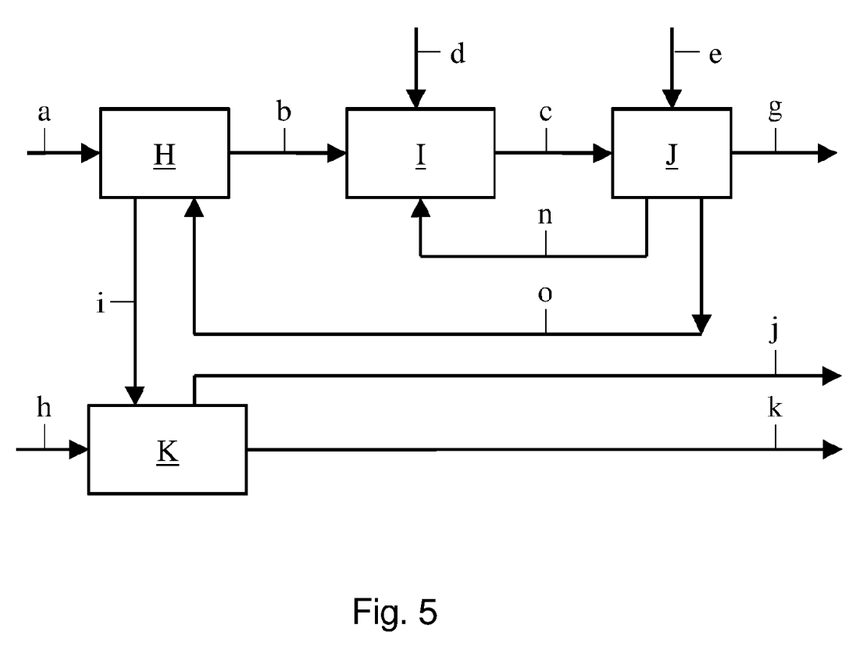

FIG. 5 is similar to FIG. 4, but herein the scrubbing liquid is recycled in two different ways. From the scrubbing section, scrubbing liquids with different concentrations of dissolved particles are extracted. The scrubbing liquid having the higher concentration of dissolved particles is recycled to the quenching section, as a quenching liquid (i.e., the first aqueous stream as applied in the process of the invention). The extracted scrubbing liquid having the lower concentration of dissolved partices is recycled to the humidification section as an aqueous stream to be fed to that section when this section also receives superheated steam (i.e., the second aqueous stream as applied in the process of the invention in the alternative b) for the humidification liquid).

Figure 6:
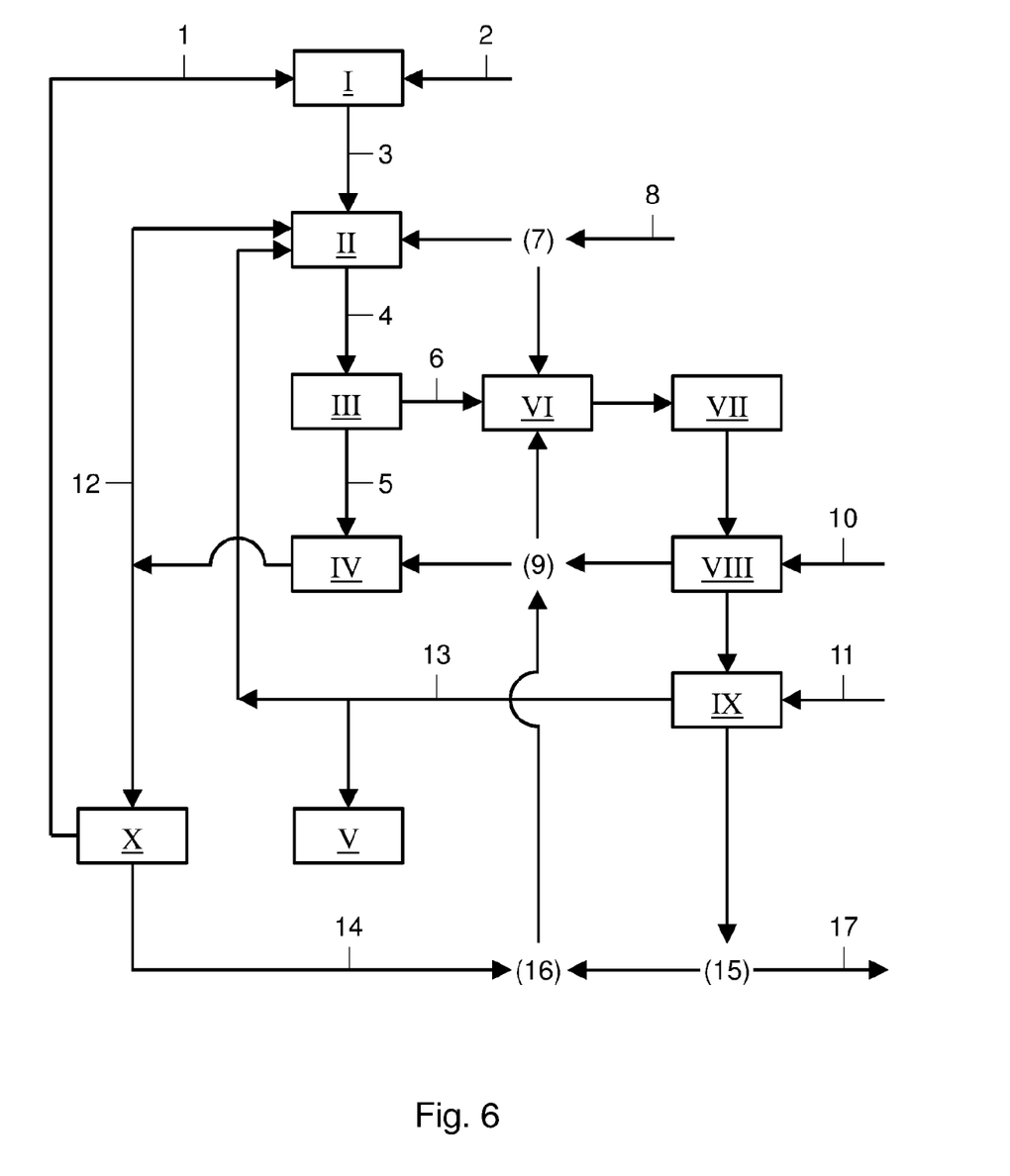

FIG. 6 refers to a preferred embodiment wherein a lean recycle solution (i.e., having a relatively low concentration of dissolved particles) is used. Therein, following a quench, humidification and coarse particulate removal processes, a lean recycle solution is combined with superheated steam in a two-phase nozzle(s) and mixed with the off gas to achieve a state of (super) saturation. Coarse particles are those having a size generally above 10 μm, which are generally considered to be non-respirable, and therewith less dangerous for people's health than particles having a size smaller than 10 μm, which can penetrate into the lungs.

This leads to condensation of water on the fine particulate matter in the gas stream. The large condensed droplets can then be removed from the off gas stream during the fine particulate and/or ammonia removal stage.

Atomization (using high pressure, ultrasound, compressed air, etc.) of the lean recycle solution into fine droplets is advantageous from the point-of-view that the atomized droplets are more easily evaporated by the added steam. In this manner, the sensible heat of the steam does not heat the off-gas (which is less preferred as this does not facilitate achieving saturation) but for evaporation of the atomized droplets. This evaporative cooling not only avoids temperature increase of the off gas, but it also generates additional water vapor, thus reducing the steam consumption even further.

The legend for FIG. 6 is as follows:
Functions:
I. Fluidised Bed Granulation;
II. Off Gas Quench & Humidification;
III. Coarse Particulate Removal;
IV. Dissolving;
V. Ammonium Salt Solution Removal;
VI. Off Gas (Super) Saturation;
VII. Fine Particulate Growth;
VIII. Fine Particulate Removal;
IX. Ammonia Removal
X. (Dedicated) Recycle Evaporation;
Streams:
1. urea melt;
2. fluidisation Gas;
3. Granulation Off Gas (Particulate+Ammonia);
4. Quenched gas;
5. Coarse particulate;
6. Quenched gas with coarse particulate removed;
7. Saturated) Steam;
8. Demineralised/Deionised Water;
9. Lean Solution;
10. Process Condensate;
11. Concentrated Solution;
12. Acidic Scrubbing Solution
13. Ammonium Salt Solution;
14. Evaporation Condensate;
15. Saturated Stack Gas;
16. Stack Condensate;
17. Emission The lean recycle solution can be derived from such sources as:
(a) steam or process condensate used for wet scrubbing of fine particulate,
(b) evaporation condensate from a dedicated evaporation process used to concentrate and recycle recovered particulate, and
(c) off gas stack condensate following a particulate removal (scrubbing) process For enhanced scrubbing performance, the lean recycle solution can be substituted by demineralized/deionized water. The main benefit of using demineralized/deionized water is seen to be related to condensation effects rather than quenching. Any impurities present in the gas stream will act as nuclei for condensation. The usage of demineralized/deionized water reduces the number of impurities added to the gas stream such that condensation occurs on the dust particles and not any additional impurities.

The invention is not limited to any particular urea production process.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

Other processes and plants include those that are based on technology such as the HEC process developed by Urea Casale, the ACES process developed by Toyo Engineering Corporation and the process developed by Snamprogetti. All of these processes, and others, may be used preceding the urea finishing method of the invention.

Urea finishing techniques, such as prilling and granulation, are known to the skilled person. Reference is made to, e.g., Ullmann's Encyclopedia of Industrial Chemistry, 2010, chapter 4.5. on urea.

The invention will be further illustrated hereinafter with reference to the Example below. The Example is not intended to limit the invention.

Example

A model was developed using flowsheeting software to study the effect of the main process parameters and show the differences between various steam injection and recycle stream options.

The results are given in Table 1 below.

In all cases the air flow to the quench is 100,000 kg/h. The relative humidity after the quench is either 80.6% or 93.5%, depending on the water concentration in the blowdown (purge), which is either 55% or 80% in this example. The relative humidity of the gas, in equilibrium with the urea/water solution, is following said water concentration. The RH of the gas in equilibrium with a 55% water/45% urea solution is 80.6%.

Case 1 represents the embodiment of FIG. 2 with saturation with steam only after quenching with the blowdown concentration fixed at 55% water.

Case 2 represents the embodiment of FIG. 2 with saturation with steam only after quenching with the blowdown concentration fixed at 80% water.

Comparison between cases 1 and 2 shows that overall steam consumption can be reduced by diluting the quenching and blowdown concentration. This has to do with the fact that after quenching, the relative humidity is already higher for case 2 than for case 1. This is by virtue of quenching with a more dilute solution, so less steam has to be added to achieve saturation. So in case 2 the temperature increase of the gas due to addition of steam is much lower and the reduction of steam required for saturation is larger than the increase of steam required for subsequent evaporation for concentration of the more dilute blowdown stream.

Case 3 represents the embodiment of FIG. 4 with saturation with steam and water with dissolved particles after quenching, with the blowdown concentration fixed at 55% water.

Case 4 represents the embodiment of FIG. 3 with saturation with steam and water without dissolved particles (demineralized water) after quenching with the blowdown concentration fixed at 55% water.

The results from cases 3 and 4 show that there is a major difference between saturation with steam only and saturation with steam and water addition. If only steam is used (cases 1 and 2), the temperature of the gas during steam addition increases. This means that the partial pressure of water increases so more steam is required to achieve saturation. Combining a second aqueous stream (with a higher water concentration than the initial quench stream) with steam for saturation of the gas (cases 3 and 4) decreases steam consumption because it avoids the temperature increase associated with steam injection alone.

When considering overall water and steam consumption of cases 3 and 4, there is minimal difference between adding water with dissolved particles to the saturation step, or adding demineralized water. Case 4 has an advantage over case 3 for particle growth in the gas stream. Any impurities present in the gas stream will act as nuclei for condensation. The usage of demineralized/deionized water reduces the number of impurities added to the gas stream such that condensation occurs on the dust particles and not any additional impurities.

Case 5 represents the embodiment of FIG. 3, with saturation with steam and water without dissolved particles (demineralized water) after quenching with the blowdown concentration fixed at 80% water.

Comparison between cases 3, 4 and 5 shows that diluting the blowdown from the quench increases the overall steam consumption. This is contrary to the comparison of cases 1 and 2, where diluting the blowdown concentration decreased the overall steam consumption.

The amount of steam required for saturation decreases for case 5 in comparison to cases 3 and 4. However, this reduction is much lower than the reduction of case 2 over case 1 because the temperature increase due to steam addition is already mitigated by injecting water in the saturation section.

The amount of steam required for evaporation/concentration is higher for case 5 than cases 3 and 4. This increase of required steam outweighs the benefit of reduced steam consumption for saturation.

TABLE 1

| | stream | parameter | unit | Saturation with steam only case 1 | Saturation with steam, more makeup water case 2 | Steam & water + dissolved particles to saturation case 3 | Steam & demin. water to saturation case 4 | Steam & demin. water to saturation, more makeup water case 5 |
|---|---|---|---|---|---|---|---|---|
| water + dissolved urea to quench | 205 | H2O | kg/h water | 2888.1 | 4097.2 | 2866.6 | 2866.8 | 4089.7 |
| steam to saturation | 222 | H2O | kg/h steam | 3115.9 | 735.8 | 1142.2 | 1142.8 | 336.4 |
| demineralized water to saturation | 221 | H2O | kg/h water | 0.0 | 0.0 | 0.0 | 84.3 | 25.5 |
| water + dissolved urea to saturation | 203 | H2O | kg/h water | 0.0 | 0.0 | 85.1 | 0.0 | 0.0 |
| temperature after quench | 102 | TEMP | ° C. | 43.5 | 41.0 | 43.4 | 43.4 | 41.0 |
| temperature after saturation | 104 | TEMP | ° C. | 48.4 | 42.2 | 43.4 | 43.4 | 41.0 |

TABLE 1-continued

| stream | param-eter | unit | Saturation with steam only case 1 | Saturation with steam, more makeup water case 2 | Steam & water + dissolved particles to saturation case 3 | Steam & demin. water to saturation case 4 | Steam & demin. water to saturation, more makeup water case 5 |
|---|---|---|---|---|---|---|---|
| water in off-gas scrubbing | 106 | H2O | kg/h water | 7750.3 | 5479.4 | 5862.9 | 5863.5 | 5105.8 |
| water in gas to quench | 101 | H2O | kg/h water | 2291.0 | 2291.0 | 2291.0 | 2291.0 | 2291.0 |
| water uptake by gas | | | kg/h water | 5459.3 | 3188.4 | 3571.9 | 3572.5 | 2814.8 |
| blowdown to evaporation section | 103 | H2O | kg/h water | 494.1 | 1617.0 | 493.9 | 494.1 | 1617.0 |
| steam consumption evaporation | 901 | H2O | kg/h steam | 664.5 | 2051.3 | 664.3 | 664.6 | 1051.4 |
| make-up water to scrubbing | 201 | H2O | kg/h water | 2837.4 | 4069.5 | 2923.6 | 2839.5 | 4069.9 |
| total water consumption | | | kg/h water | 5953.4 | 4805.4 | 4065.8 | 4066.6 | 4431.8 |
| LP steam consumption, total | | | kg/h steam | 3780.4 | 2787.1 | 1806.5 | 1807.4 | 2387.8 |
| water balance | | | kg/h water | 0.0 | 0.0 | 0.0 | 0.0 | 0.0 |

The invention claimed is:

1. A method for removing urea dust particles from a gas stream obtained from a finishing section of a urea production plant, the method comprising
    (a) quenching said gas stream using a first aqueous stream as a quenching liquid so as to create a quenched gas stream;
    (b) mixing said quenched gas stream with a humidification fluid which is either saturated steam or superheated steam mixed with a second aqueous stream, so as to produce a humidified gas stream, and
    (c) subjecting said humidified gas stream to particle separation by means of a scrubbing liquid in which at least part of the urea dust particles in the gas stream are soluble, wherein the particle separation comprises one or more venturi scrubbing steps using said scrubbing liquid.

2. The method according to claim 1, wherein the first aqueous stream comprises dissolved urea dust particles.

3. The method according to claim 2, wherein the first aqueous stream comprises an aqueous stream recycled from the scrubbing liquid used in the particle separation step (c).

4. The method according to claim 3, wherein in step (b) the humidification fluid comprises superheated steam mixed with a second aqueous stream, and wherein the second aqueous stream has a lower concentration of dissolved particles than the first aqueous stream.

5. The method according to claim 1, wherein in step (b) the humidification fluid comprises superheated steam mixed with a second aqueous stream, and wherein the second aqueous stream has the same composition as the first aqueous stream.

6. The method according to claim 1, wherein the first aqueous stream has a temperature of below 45° C., wherein the particle separation of step (c) comprises one or more venturi scrubbing steps, and wherein the amount of steam is 0.5-5% relative to the amount of gas.

* * * * *